(12) United States Patent
Delap

(10) Patent No.: US 8,906,003 B2
(45) Date of Patent: Dec. 9, 2014

(54) ERODIBLE EMBOLIZATION MATERIAL FOR TARGETED TUMOR CRYOABLATION

(75) Inventor: Dennis Delap, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 371 days.

(21) Appl. No.: 13/488,988

(22) Filed: Jun. 5, 2012

(65) Prior Publication Data

US 2013/0324988 A1 Dec. 5, 2013

(51) Int. Cl.
*A61B 18/18* (2006.01)

(52) U.S. Cl.
USPC .................................................. 606/21

(58) Field of Classification Search
CPC ............... A61B 18/02; A61B 2018/02; A61B 2018/0212; A61B 2018/0293
USPC .................................................. 606/21
See application file for complete search history.

(56) References Cited

U.S. PATENT DOCUMENTS

| | | | |
|---|---|---|---|
| 5,538,726 | A | 7/1996 | Order |
| 5,780,044 | A | 7/1998 | Yewey et al. |
| 5,899,897 | A | 5/1999 | Rabin et al. |
| 5,906,209 | A | 5/1999 | Tortal et al. |
| 7,094,230 | B2 | 8/2006 | Flaherty et al. |
| 7,833,187 | B2 | 11/2010 | LePivert et al. |
| 2002/0192289 | A1 | 12/2002 | Zheng et al. |
| 2005/0196449 | A1 | 9/2005 | Dicarlo et al. |
| 2005/0214268 | A1 | 9/2005 | Cavanagh, III et al. |
| 2007/0031338 | A1* | 2/2007 | Zabinski ............... 424/9.6 |
| 2007/0141339 | A1 | 6/2007 | Song et al. |
| 2008/0140061 | A1 | 6/2008 | Toubia et al. |
| 2009/0092677 | A1 | 4/2009 | Richard |
| 2009/0198093 | A1 | 8/2009 | Meissner et al. |
| 2011/0160514 | A1 | 6/2011 | Long et al. |

FOREIGN PATENT DOCUMENTS

| | | |
|---|---|---|
| WO | WO 2005/084645 A | 9/2005 |
| WO | WO 2005/097677 A1 | 10/2005 |

OTHER PUBLICATIONS

Liu et al., << Novel polymeric microspheres containing norcantharidin for chemoembolization >>, Journal of Controlled Release, Elsevier, Amsterdam, NL, Nov. 25, 2006 (pp. 35-41) Abstract Only.

* cited by examiner

*Primary Examiner* — Robert N Wieland
(74) *Attorney, Agent, or Firm* — Brinks Gilson & Lione

(57) ABSTRACT

A method of cryoablating diseased tissue is provided. The method includes providing an embolization agent. The embolization agent includes an inner core made of a first material. The inner core has a diameter less than a diameter of an opening of a target vessel. The embolization agent further includes an erodible outer shell made of a second embolization material encompassing the inner core. The erodible outer shell has an initial diameter greater than the diameter of the opening to occlude the target vessel. The method further includes occluding the opening of the target vessel with the embolization agent to reduce blood flow in the diseased tissue. The method further includes cryoablating the diseased tissue with a cryoablation probe while the target vessel is occluded by the embolization agent.

22 Claims, 4 Drawing Sheets

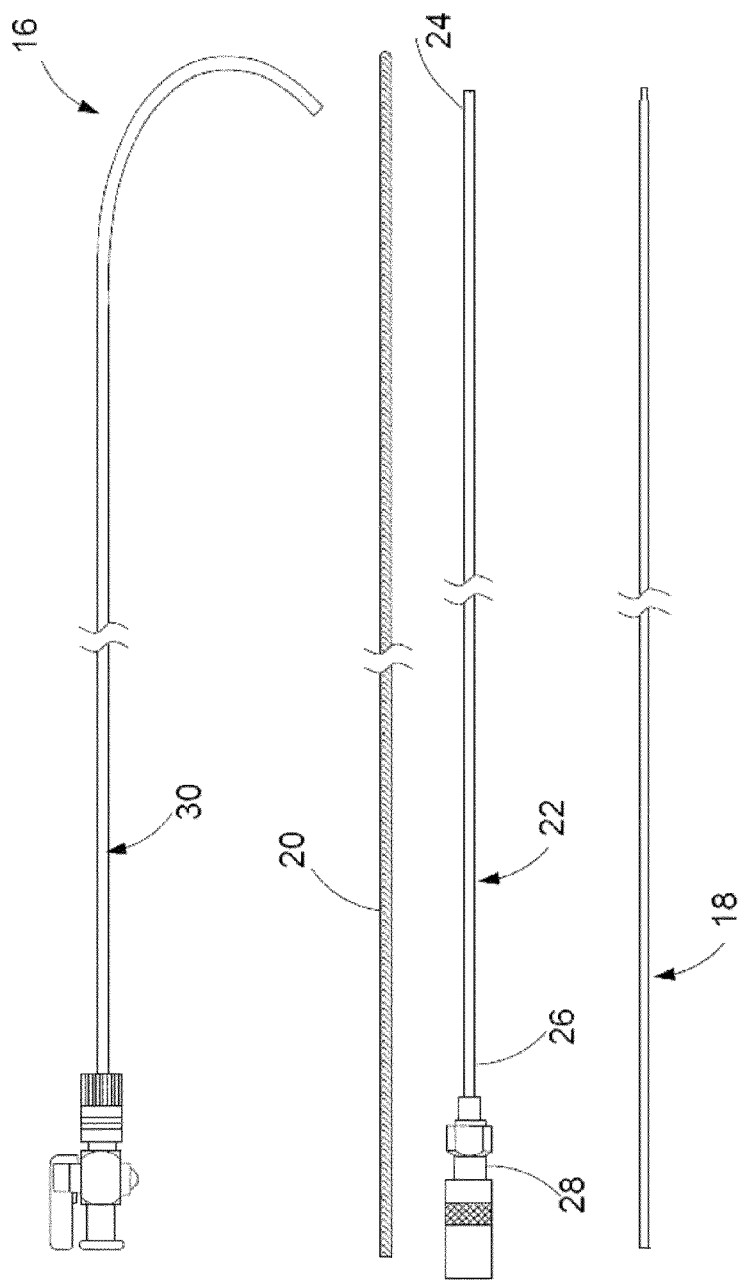
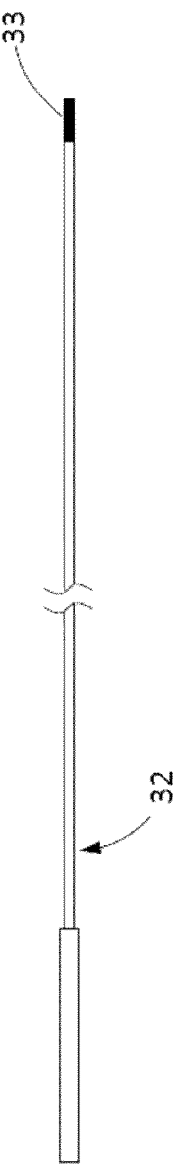
FIG. 2A
FIG. 2B

ERODIBLE EMBOLIZATION MATERIAL FOR TARGETED TUMOR CRYOABLATION

BACKGROUND OF THE INVENTION

1. Field of the Invention

The present disclosure generally relates to cryoablation procedures. More specifically, the present disclosure relates to the use of an embolization agent in a cryoablation procedure.

2. Background

Cryoablation is an effective treatment method for localized cancerous tumors. Cryoablation probes (cryoprobes) are cooled, thermally conductive needles with chilled tips which remove heat from tissue in contact with the cryoablation probe.

Cryoablation is especially effective for tumors in kidneys, where healthy tissue surrounding a tumor has a higher blood flow rate than that of the tumor tissue. The healthy tissue's increased blood flow allows it to survive cryoablation tissue more easily than the tumor tissue. Successful treatment and thawing converts the tumor tissue into an inert necrotic abscess which eventually assimilates into the body.

However, cryoablation is less effective in treating cancerous tumors in most other organs other than kidneys, because tumor tissue in these organs generally has higher blood flow than in surrounding tissue. As a result, there is risk of significant damage to healthy tissue, and increased blood flow at the edges of the tumor can protect the remaining cancerous tissue from cryoablation.

SUMMARY

In overcoming the drawbacks and other limitations of the related art, the present disclosure provides an erodible embolization agent which decreases blood flow in tumor tissue relative to blood flow in surrounding healthy tissue just prior to or during cryoablation. As a result, cryoablation is more effective for a broader range of tumor tissues, including those in which blood flow is otherwise greater than in surrounding healthy tissue. Additionally, the survival rate of surrounding healthy tissue after cryoablation is improved.

In some embodiments, the present disclosure relates to a method of cryoablating diseased tissue. The method includes providing an embolization agent. The embolization agent includes an inner core made of a first material. The inner core has a diameter less than a diameter of an opening of a target vessel. The embolization agent further includes an erodible outer shell made of a second embolization material encompassing the inner core. The erodible outer shell has an initial diameter greater than the diameter of the opening to occlude the target vessel. The method further includes occluding the opening of the target vessel with the embolization agent to reduce blood flow in the diseased tissue. The method further includes cryoablating the diseased tissue with a cryoablation probe while the target vessel is occluded by the embolization agent.

In some embodiments, the present disclosure relates to a method of cryoablating diseased tissue. The method includes providing an embolization agent. The embolization agent includes an inner core made of a first material. The inner core has a diameter less than a diameter of an opening of a healthy vessel adjacent to a diseased vessel located in the diseased tissue. The embolization agent further includes an erodible outer shell made of a second embolization material encompassing the inner core. The erodible outer shell has an initial diameter less than a diameter of an opening of the diseased vessel and greater than the diameter of the opening of the healthy vessel to occlude the healthy vessel. The method further includes occluding the opening of the healthy vessel with the embolization agent to reduce blood flow in the diseased tissue. The method further includes cryoablating the diseased tissue with a cryoablation probe while the healthy vessel is occluded by the embolization agent. The method further includes allowing the erodible outer shell to erode at a predetermined rate.

In some embodiments, the present disclosure relates to a method of cryoablating diseased tissue. The method includes providing an introducer apparatus. The method further includes providing an embolization agent. The embolization agent includes an inner core made of a first material. The inner core has a diameter less than a diameter of an opening of a target vessel. The embolization agent further includes an erodible outer shell made of a second embolization material encompassing the inner core. The erodible outer shell has an initial diameter greater than the diameter of the opening to occlude the target vessel. The method further includes occluding the opening of the target vessel with the embolization agent to reduce blood flow in the diseased tissue. The method further includes introducing with the introducer apparatus the embolization agent to the opening of the target vessel. The method further includes occluding the opening of the target vessel with the embolization agent to reduce blood flow in the diseased tissue. The method further includes cryoablating the diseased tissue with a cryoablation probe while the target vessel is occluded by the embolization agent.

Further features and advantages of the present disclosure will become apparent from consideration of the following description and the appended claims when taken in connection with the accompanying drawings. It should be understood that the description and specific examples are intended for purposes of illustration only and are not intended to limit the scope of the present disclosure.

BRIEF DESCRIPTION OF THE DRAWINGS

FIG. 2A is a side view of an introducer apparatus including a wire guide, catheter, needle, and introducer sheath for use with an embolization agent;

FIG. 2B is a side view of a cryoablation probe for use in a cryoablation procedure;

Figure 1:
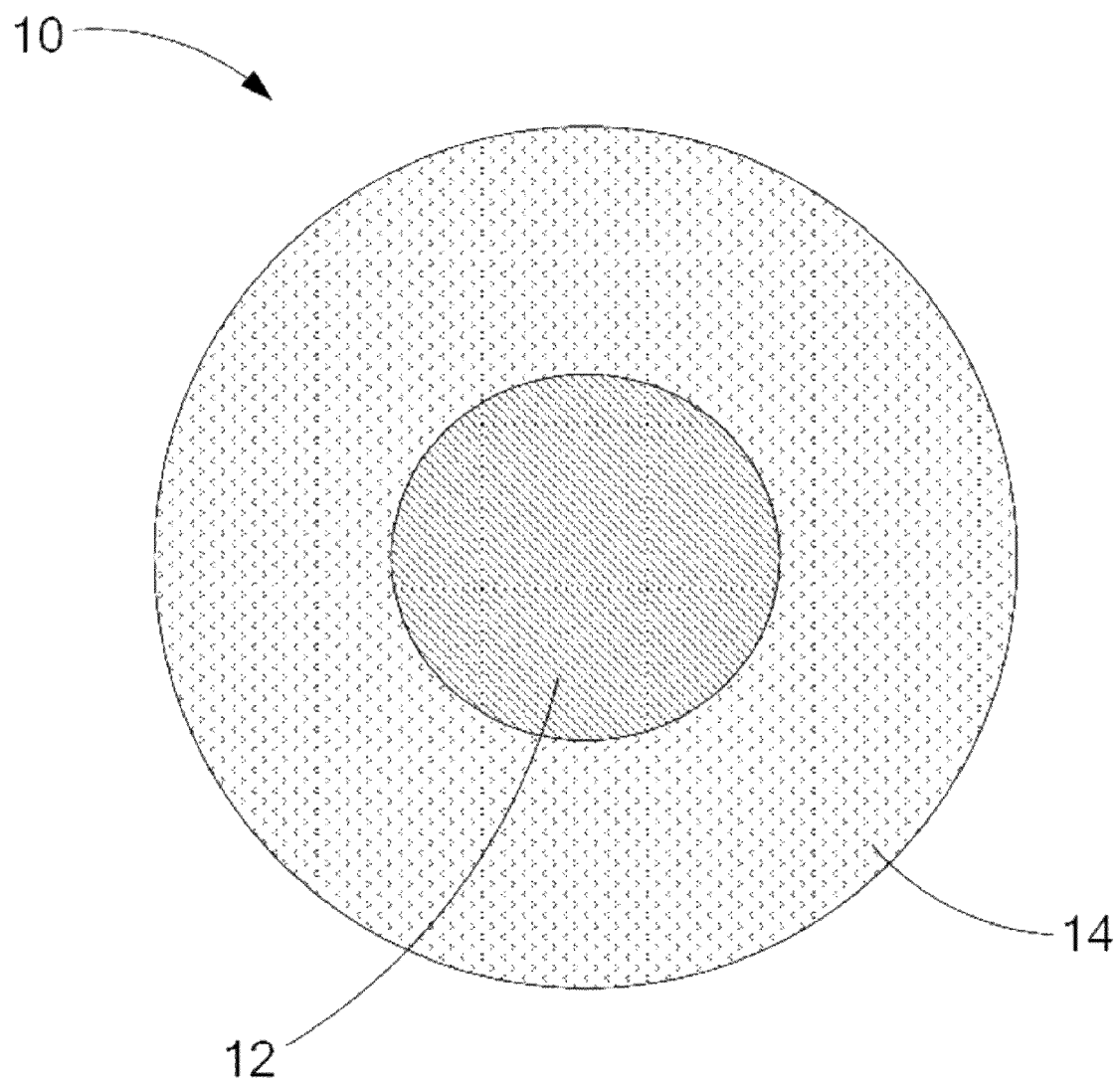
FIG. 1 is a cross-sectional view of an erodible embolization agent.

The drawings described herein are for illustration purposes only and are not intended to limit the scope of the present disclosure in any way.

DETAILED DESCRIPTION

The following description is merely exemplary in nature and is in no way intended to limit the present disclosure or its application or uses. It should be understood that throughout the description and drawings, corresponding reference numerals indicate like or corresponding parts and features.

FIG. 1 illustrates an embolization agent 10 (i.e. embolization material) comprising an inner core 12 made of a fast dispersing material that has a diameter less than a predetermined size for an initial opening in a target vessel and an outer shell 14 made of an embolization material that encompasses the inner core 12 and has an initial diameter that will occlude the initial opening in the target vessel. In some embodiments, the outer shell 14 erodes at a predetermined rate to enhance penetration of the embolization agent 10 into the opening of the target vessel. Upon becoming exposed by the erosion of the outer shell 14, the inner core 12 preferably disperses rapidly into the target vessel within a matter of seconds to hours without obstructing subsequent blood flow. Target vessels may be fluid-transfer vessels, including but not limited to vascular or lymphatic vessels.

In this embodiment, the outer shell 14 of embolization material erodes at a predetermined rate that is predictable and controllable. By erosion, the embolization material may become disassembled, digested, or metabolized into smaller or dispersed molecules through the action of the surrounding environment present in the targeted tissues vessels. Eroded embolization material may form fragments that will continue to erode. These erodible fragments of embolization material are smaller than the size expected to cause a stroke or any other type of complication in the patient.

This predetermined rate of erosion results in substantial erosion of the outer shell 14 in a timeframe of about 30 seconds to 24 hours, or about 5 minutes to an hour, or about 5 minutes to 30 minutes, or about 10 minutes to 20 minutes, or about 15 minutes. Upon substantial erosion of the outer shell 14, the inner core 12 is able to disperse into the target vessel. The properties of the embolization material may be adjusted to be suitable for use with vascular, lymphatic, or other fluid-transfer vessels. In addition, the outer shell 14 of embolization material may erode at a similar rate when in contact with the vessel walls or when in contact with a fluid located in the vessels. Maintaining a similar rate of erosion during treatment assists in keeping the embolization effect substantially constant as the embolization agent 10 progresses through smaller and smaller vessels.

The outer shell 14 may be comprised of a single layer or multiple layers that are different or similar in composition. The single layer or each of the multiple layers may be selected from any suitable embolization material known in the art, for example a bioerodible material. In some examples, the material can be polylactic acid, polyvinyl alcohol, tris-acryl gelatin microshells, gelatin sponge microfibrillar collagen, ethoiodized oil, autologous materials, celluloses, polyacrylic acids, polyacylamides, and alginates or mixtures thereof. The embolization material may be multi-component, for example it may include a polymer solution and a gelling precursor. The outer shell 14 of embolization material 10 may further comprise anti-thrombogenic agents to prevent eroded fragments from clotting as the fragments disperse.

The material of the inner core 12 may be any fast dissolving or dispersing solid or liquid material that does not adversely affect the body known to one skilled in the art including but not limited to sugar, sucrose, lactose, fructose, salt, or any fast dissolving or dispersing polymer known in the art. The inner core may be ionically or covalently bonded to the embolization material of the outer shell 14 or held in place by entanglement, van der Waal forces, hydrogen bonding, or any other means known to one skilled in the art of particle encapsulation. Optionally, the inner core 12 may expand upon freezing.

In some examples, the materials of the inner core 12 are obtained from compression or suspension/emulsion polymerization. The outer shell 14 may be applied through a fluid bed coating process like Wurster coating.

In some examples, after the outer shell 14 has eroded, the material of the inner core 12 may immediately dissolve and disperse into the target vessel. The material of the inner core 12 may be two-phase system to facilitate dissolving and dispersal. In some examples, upon the material of the inner core 12 may expand upon freezing, causing the outer shell 14 to contact a vessel wall and shatter, after which the material of the inner core 12 dissolves and disperses.

In some embodiments, the embolization agent 10 may have a spherical, ellipsoidal, non-spherical, or non-ellipsoidal shape. However, some sort of symmetry is preferred to obtain a uniform and predictable erosion rate. Since the embolization agent 10 will be disposed within blood vessels having a circular cross-section, the symmetry is preferably at least radial to obtain consistent embolization time intervals. For example, the embolization agent 10 may take the shape of a shell or ellipsoid with two axes having a length approximately equal to one another and a third axis greater than the other two, i.e., football-shaped without the pointed ends. Shaping of the embolization agent 10 may occur during or after formation of the embolization agent 10 using any process known to one skilled in the art, such as molding, compression, or agglomeration, among others.

In some embodiments, one or both of the inner core 12 and outer shell 14 may further comprise a radiopaque material. The radiopaque material may be discrete particles or a coating. The radiopaque material may be a polymer, ceramic, or a noble metal. Examples of noble metals include gold, platinum, iridium, palladium, or rhodium, or a mixture thereof. The radiopaque material provides enhanced fluoroscopy to more easily identify the location of the embolization agent 10 during delivery.

FIG. 2A depicts an introducer apparatus 16 for introducing one or more embolization agents 10 into body tissue. The introducer apparatus 16 includes a hollow needle 18 to pierce the patient's skin and enter the body tissue at an angle with respect thereto. A wire guide 20 is then inserted into the hollow needle 18 and is advanced percutaneously into the body tissue to the desired position for delivery of the embolization agent 10 to the target vessels. The hollow needle 18 is then pulled in a backward direction so as to be removed from the body tissue and from contact with the wire guide. Next, a catheter 22 is advanced along the wire guide 20 to the desired position.

The catheter 22 has a distal end 24 through which the embolization agent 10 is delivered into the target vessels. The catheter is preferably made of a soft, flexible material such as silicon or any other suitable material. Generally, the catheter also has a proximal end 26 and a plastic adaptor 28 to receive the embolization agent 10. The diameter of the catheter is based upon the size of the body tissue into which the catheter is inserted and the amount of embolization agent 10 to be delivered. The inner diameter of the catheter 22 is greater than the diameter of the outer shell 14 of the embolization agent 10 to allow delivery of the agent to the target vessel.

The introducer apparatus 16 may further include a polytetrafluoroethylene (PTFE) introducer sheath 30 to assist the percutaneous introduction of the wire guide 20 and the catheter 22 in the body tissue. Of course, any other suitable material may be used for the sheath 30. The introducer sheath 30 facilitates inserting the catheter 22 percutaneously to a desired location in the body tissue, and provides stability to the catheter 22.

FIG. 2B depicts a cryoablation probe 32 for cryoablating diseased tissue. However, any cryoablation probe or cryoablation technique may be used without falling outside the scope of the present disclosure. The cryoablation probe 32 has a chilled tip 33 configured to freeze tissue on contact.

Figure 3A:
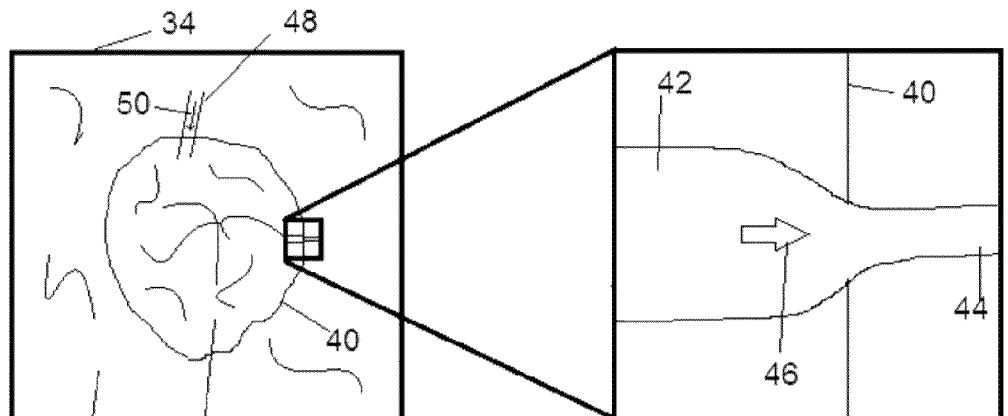
FIG. 3A is an environmental view of body tissue before embolization and cryoablation treatments begin.

FIGS. 3A-3F illustrate steps in a cryoablation procedure using the embolization agent 10. FIG. 3A illustrates an environmental view of body tissue 34 before embolization and cryoablation treatments begin. The body tissue 34 may be any tissue or organ in the body, for example a liver. The body tissue 34 has diseased tissue 36 and healthy, non-diseased tissue 38 surrounding or adjacent to the diseased tissue 36. The diseased tissue 36 may be a cancerous tumor, for example. The healthy tissue 20 and the diseased tissue 36 meet at a boundary 40. As shown in the magnified portion of the body tissue 34 at the boundary 40, the diseased tissue 36 contains diseased vessels 42 and the healthy tissue 38 contains healthy vessels 44. The vessels 42, 44 may be fluid-transfer vessels, including but not limited to vascular or lymphatic vessels. The direction of downstream blood flow is indicated by arrow 46.

In some examples, the diameter of the outer shell 14 of embolization material is typically less than about 100 micrometers but greater than about 80 micrometers or 85 micrometers, while the diameter of the inner core 12 of fast dispersing material is preferably less than about 40 micrometers or 35 micrometers. By comparison, liver tumor vasculature vessels have an opening on the order of about 40 to 80 micrometers, while normal healthy liver tissue has vascular vessels with openings between about 7 to 40 micrometers. Thus, the outer shell 14 has a diameter that is slightly greater than the initial opening in the targeted vessels, while the inner core 12 has a diameter either the same or slightly smaller than the expected size of the opening in the targeted vessels. The exact size of the openings associated with other vascular or lymphatic tissue vessels may vary from the above description. Such variation is contemplated to be within the scope of the present invention.

In this example, the diseased vessels 42 have greater diameters than the surrounding healthy vessels 44, as is common for many types of diseased tissue 36 surrounded by healthy tissue 38. In some examples, large vessels 48 may allow blood to flow into the diseased tissue 36 from the healthy tissue 38 in a downstream direction as indicated by arrow 50. However, because of blockages caused by the diseased tissue 36, there may be no corresponding large vessel allowing outflow of the blood that flowed into the diseased tissue 36 through large vessels 48.

Figure 3B:
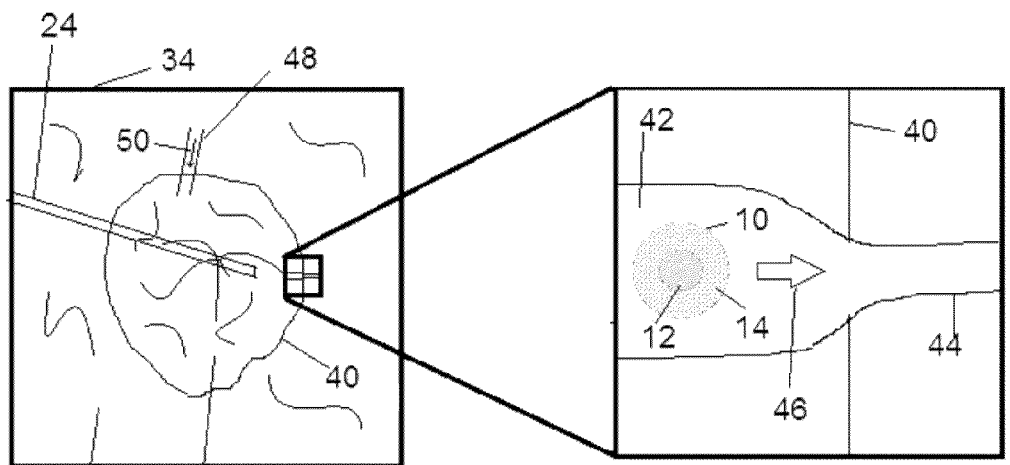
FIG. 3B is an environmental view of body tissue as the embolization agents are introduced in the body tissue.

FIG. 3B illustrates an environmental view of body tissue 16 as the embolization agents 10 are introduced in the body tissue 34. The embolization agents 10 may be placed in the catheter 22 prior to or after insertion of the catheter 22 into the body tissue 34. When the distal end 24 of the catheter 22 is at a location near the target vessel, the embolization agents 10 is advanced through the catheter 22 preferably from the proximal end 26 and distally beyond the distal end 24 of the catheter 22 to a location within the body tissue 34 near or at the target vessel. A shaft or pusher member advances the embolization agents 10 through the catheter 22. Alternatively or additionally, the embolization agents 10 can be suspended in and premixed in a solution which may include saline and which is advanced through the catheter 22 and into the body tissue 34 by a fluid delivery apparatus, optionally in combination with the shaft or pusher member.

In some examples, the target vessels in which the embolization agents 10 are introduced may one or more diseased vessels 44 throughout the diseased tissue 36, including the interior of the diseased tissue 36 and near the boundary 40. In other examples, the target vessels in which the embolization agents 10 are introduced are large vessels 48 located in healthy tissue 38. In some examples, embolization agents 10 can be introduced in all of the above locations in a single procedure. Regardless of where the embolization agents 10 are introduced, the embolization agents 10 flow downstream in the direction of arrow 48 until they reach the boundary 40.

Figure 3C:
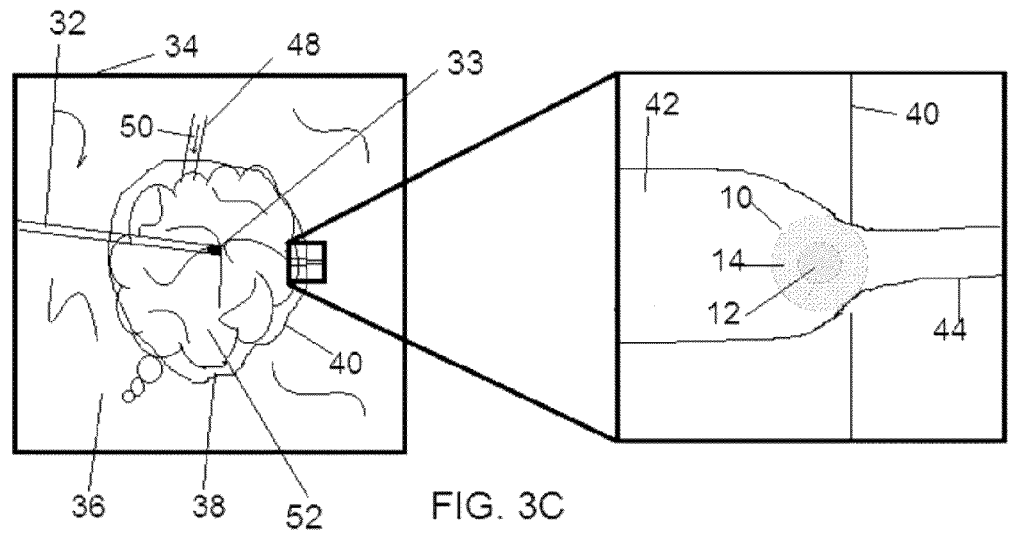
FIG. 3C is an environmental view of body tissue as the embolization agents become lodged at the boundary between the diseased and healthy vessels and the diseased tissue is cryoablated.

FIG. 3C illustrates an environmental view of body tissue 16 as the embolization agents 10 become lodged at the boundary 40 between the diseased vessels 42 and healthy vessels 44, during which time the diseased tissue 36 is cryoablated. The embolization agents 10 occlude the boundary 40 and are prevented from passing into the healthy vessels 44 because the diameter of the outer shells 14 is greater than the diameter of the healthy vessels 44. Additionally, because large outflow vessels corresponding to the large inflow vessels 48 may be blocked, embolization agents 10 introduced into the large inflow vessels 48 may not have a large diameter vessel through which to escape the diseased tissue 36, and will instead become lodged at the boundary 40 of the smaller vessels 42, 44.

Because of the lodged embolization agents 10, the diseased tissue 36 experiences reduced or stopped blood flow in the entire diseased tissue 36 or around the boundary 40. In body tissue 34 where diseased tissue 36 normally experiences greater blood flow than the surrounding healthy tissue 38, the blood flow in the diseased tissue 36 is preferably reduced sufficiently to be lesser than the blood flow in the surrounding healthy tissue 38.

In embodiments where the embolization agents 10 include radiopaque material, fluoroscopy helps determine when blood flow has been reduced. Specifically, agglomeration of embolization agents 10 around the boundary 40, as viewed by the practitioner using a fluoroscope, indicates reduction in blood flow.

Once the embolization agents 10 are lodged at the boundary 40, the cryoablation probe 32 is inserted into the diseased tissue 36. The cryoablation probe 32 can be used to ablate the diseased tissue 36 at its in interior, and the diseased tissue 36 near and/or at the boundary 40. In some examples, the cryoablation probe 32 can be used to create an ice ball 52 that expands throughout the diseased tissue 36 until it reaches the boundary 40. Since, due to embolization, the healthy tissue 38 has a greater blood flow than the diseased tissue 36, the healthy tissue 36 is more resistant to the cryoablation procedure, and there is less risk of destroying the healthy tissue 36. In the optional embodiment where the inner core 12 expands upon freezing (not shown), the embolization agent 10 may embolize the boundary 40 during cryoablation but immediately cease to embolize the boundary 40 after thawing. Thus the healthy tissue 36 adjacent the boundary 40 is further protected.

Once cryoablation is complete, the diseased tissue 36 is destroyed and becomes a necrotic abscess, the cryoablation probe 32 is removed, and the necrotic abscess thaws. The cryoablation procedure may be timed to ensure completion before the embolization agents 10 erode sufficiently to disperse in the healthy vessels 44.

Figure 3D:
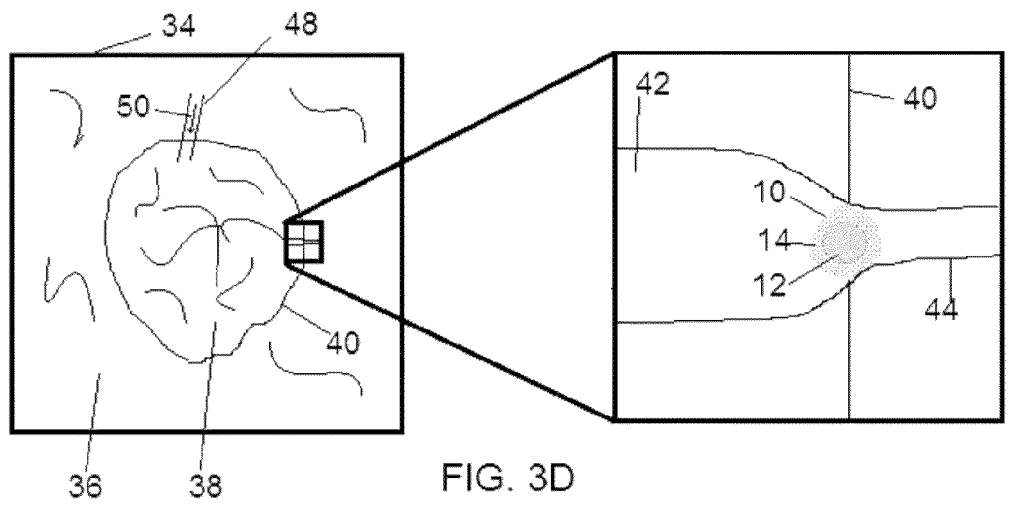
FIG. 3D is an environmental view of body tissue after cryoablation and thawing of the diseased tissue are complete and as the embolization agents are eroding.

FIG. 3D illustrates an environmental view of body tissue 16 after cryoablation and thawing of the diseased tissue 36 are complete and as the embolization agents 10 are allowed to erode at a predetermined rate to expose the inner cores 12.

Figure 3E:
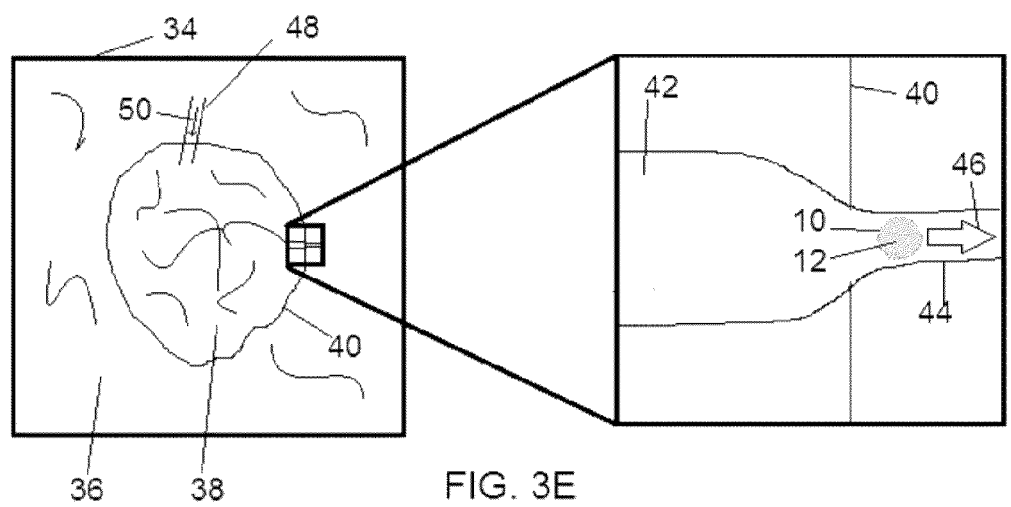
FIG. 3E is an environmental view of body tissue after the outer shells have eroded and as the inner cores are dispersing.

FIG. 3E illustrates an environmental view of body tissue 16 after the outer shells 14 have substantially or fully eroded, and thus the inner cores 12 are dispersing along the blood flow gradient 46 into the healthy vessels 44. Once the inner cores 12 disperse, the surrounding healthy tissue 38 assimilates the necrotic abscess.

The effective concentration or dosage of the embolization agent 10 can be determined and varied by the physician treating the patient. Such a decision should be based on the nature, severity, and location of the condition to be treated, the extent of desired reduction in blood flow or reduction in blood flow necessary for successful cryoablation, and the method selected to administer the embolization agent 10. Any means known to one skilled in the art may be used to introduce an acceptable dosage of the embolization agent 10 to the target vessel.

A person skilled in the art will recognize from the previous description that modifications and changes can be made to the present disclosure without departing from the scope of the disclosure as defined in the following claims.

What is claimed is:

1. A method of cryoablating diseased tissue, the method comprising:
    providing an embolization agent, the embolization agent comprising:
        an inner core made of a first material, the inner core having a diameter less than a diameter of an opening of a target vessel; and
        an erodible outer shell made of a second embolization material encompassing the inner core and having an initial diameter greater than the diameter of the opening to occlude the target vessel;
    occluding the opening of the target vessel with the embolization agent to reduce blood flow in the diseased tissue; and
    cryoablating the diseased tissue with a cryoablation probe while the target vessel is occluded by the embolization agent.

2. The method of claim 1 further comprising allowing the erodible outer shell to erode at a predetermined rate.

3. The method of claim 2 wherein the erodible outer shell of the second embolization material erodes at a similar rate when in contact with the target vessel or when in contact with a fluid located in the target vessel.

4. The method of claim 2 wherein the inner core of the first material disperses into the target vessel after becoming exposed by the erosion of the second embolization material of the erodible outer shell.

5. The method of claim 2, wherein after erosion, any existing fragments of the second embolization material are smaller than the size expected to cause a stroke or other type of complication in the patient.

6. The method of claim 2 wherein the predetermined rate of erosion for the outer shell of the second embolization material results in substantial erosion of the outer shell in a timeframe of about 30 seconds to 24 hours.

7. The method of claim 1 further comprising introducing the embolization agent in a diseased vessel in the diseased tissue.

8. The method of claim 7 wherein a diameter of the diseased vessel is greater than the diameter of the opening of the target vessel, the erodible shell being less than the diameter of the diseased vessel.

9. The method of claim 7 wherein the target vessel is connected to the diseased vessel, the target vessel being disposed in non-diseased tissue that is adjacent to the diseased tissue.

10. The method of claim 1 further comprising introducing the embolization agent in the target vessel, the target vessel being disposed in non-diseased tissue that is adjacent to the diseased tissue.

11. The method of claim 1 wherein the diameter of the core material depends on the temperature of the core material.

12. The method of claim 11 wherein a decrease in the temperature of the core material caused by cryoablation causes the diameter of the core material to increase to embolize the target vessel.

13. The method of claim 12 wherein an increase in temperature of the core material caused by thawing after cryoablation causes the diameter of the core material to decrease to stop embolizing the target vessel.

14. The method of claim 1 wherein the blood flow in the diseased tissue is reduced relative to blood flow in non-diseased tissue that is adjacent to the diseased tissue.

15. The method of claim 1 wherein the initial diameter of the erodible outer shell of the second embolization material is less than about 100 micrometers and the diameter of the inner core of the first material is less than about 40 micrometers.

16. The method of claim 1 wherein the first material of the inner core is one of sugar, sucrose, lactose, fructose, salt, fast dispersing polymers, or mixtures thereof.

17. The method of claim 1 wherein the second embolization material of the erodible outer shell is one of polylactic acid, polyvinyl alcohol, tris-acryl gelatin microshells, gelatin sponge microfibrillar collagen, ethoiodized oil, autologous materials, celluloses, polyacrylic acids, polyacylamides, alginates, or mixtures thereof.

18. The method of claim 1 wherein at least one of the inner core and erodible outer shell further comprises a radiopaque material.

19. A method of cryoablating diseased tissue, the method comprising:
    providing an embolization agent, the embolization agent comprising:
        an inner core made of a first material, the inner core having a diameter less than a diameter of an opening of a healthy vessel adjacent to a diseased vessel located in the diseased tissue; and
        an erodible outer shell made of a second embolization material encompassing the inner core and having an initial diameter less than a diameter of an opening of the diseased vessel and greater than the diameter of the opening of the healthy vessel to occlude the healthy vessel;
    occluding the opening of the healthy vessel with the embolization agent to reduce blood flow in the diseased tissue;
    cryoablating the diseased tissue with a cryoablation probe while the healthy vessel is occluded by the embolization agent; and
    allowing the erodible outer shell to erode at a predetermined rate.

20. A method of cryoablating diseased tissue, the method comprising:
    providing an introducer apparatus;
    providing an embolization agent, the embolization agent comprising:
        an inner core made of a first material, the inner core having a diameter less than a diameter of an opening of a target vessel; and
        an erodible outer shell made of a second embolization material encompassing the inner core and having an initial diameter greater than the diameter of the opening to occlude the target vessel;

introducing with the introducer apparatus the embolization agent to the opening of the target vessel;

occluding the opening of the target vessel with the embolization agent to reduce blood flow in the diseased tissue; and cryoablating the diseased tissue with a cryoablation probe while the target vessel is occluded by the embolization agent.

21. The method of claim 20 wherein the introducer apparatus is a fluid delivery apparatus, wherein the fluid delivery apparatus introduces into the targeted tissue vessel of the patient a solution premixed with the embolization agent, wherein the solution includes saline.

22. The method of claim 20 wherein the introducer apparatus comprises:

a hollow needle to pierce the patient's body;

a wire guide for insertion into the hollow needle with percutaneous advancement into the patient's body to the desired targeted tissue vessel allowing for the subsequent removal of the hollow needle;

a catheter having a proximal and distal end, the catheter advanced along the wire guide to the target vessel allowing for removal of the wire guide; and a pusher member to advance the embolization agent from the proximal end of the catheter through the distal end of the catheter into the target vessel.

* * * * *